US008611015B2

(12) United States Patent
Wheeler et al.

(10) Patent No.: US 8,611,015 B2
(45) Date of Patent: Dec. 17, 2013

(54) USER INTERFACE

(75) Inventors: Aaron Joseph Wheeler, San Francisco, CA (US); Luis Ricardo Prada Gomez, Hayward, CA (US); Hayes Solos Raffle, Palo Alto, CA (US)

(73) Assignee: Google Inc., Mountain View, CA (US)

( * ) Notice: Subject to any disclaimer, the term of this patent is extended or adjusted under 35 U.S.C. 154(b) by 139 days.

(21) Appl. No.: 13/302,916

(22) Filed: Nov. 22, 2011

(65) Prior Publication Data

US 2013/0128364 A1     May 23, 2013

(51) Int. Cl.
*G02B 27/14*      (2006.01)
*G03H 1/00*       (2006.01)

(52) U.S. Cl.
USPC .......................................... 359/630; 359/13

(58) Field of Classification Search
USPC .................... 359/630–633, 13; 351/200–246
See application file for complete search history.

(56) References Cited

U.S. PATENT DOCUMENTS

| | | | |
|---|---|---|---|
| 6,307,526 | B1 | 10/2001 | Mann |
| 2002/0180799 | A1 | 12/2002 | Peck et al. |
| 2003/0020755 | A1 | 1/2003 | Lemelson et al. |
| 2003/0098954 | A1* | 5/2003 | Amir et al. ................... 351/210 |
| 2004/0174496 | A1* | 9/2004 | Ji et al. .......................... 351/209 |
| 2006/0082542 | A1 | 4/2006 | Morita et al. |
| 2006/0110008 | A1* | 5/2006 | Vertegaal et al. ............ 382/103 |

FOREIGN PATENT DOCUMENTS

| | | | |
|---|---|---|---|
| KR | 10-2004-0027764 A | 4/2004 |
| KR | 10-2010-0006652 A | 1/2010 |

OTHER PUBLICATIONS

Gilson, et al., An automated calibration method for non-see-through head mounted displays, Journal of Neuroscience Methods, vol. 199, Issue 2, Apr. 28, 2011, 16 pages.
Borah, Technology and Application of Gaze Based Control, presented at the RTO Lecture Series on "Alternative Control Techniques: Human Factors Issues", and published by NATO Research & Technology Organisation in RTO-EN-3, Oct. 1998, 10 pages.
Arrington Research, ViewPoint EyeTracker, Software User Guide, May 28, 2009, Scottsdale, Arizona, 248 pages.
Lastra, et al., Course Notes, Programming Virtual Worlds, SIGGRAPH 97, Aug. 8, 1997, Los Angeles, California, 277 pages.
PCT Search Report and Written Opinion, PCT International Application No. PCT/US2012/062933 dated May 15, 2013.

\* cited by examiner

*Primary Examiner* — Mohammed Hasan
(74) *Attorney, Agent, or Firm* — McDonnell Boehnen Hulbert & Berghoff LLP

(57) ABSTRACT

A head-mounted display (HMD) may include an eye-tracking system, an HMD-tracking system and a display configured to display virtual images. The virtual images may present an augmented reality to a wearer of the HMD and the virtual images may adjust dynamically based on HMD-tracking data. However, position and orientation sensor errors may introduce drift into the displayed virtual images. By incorporating eye-tracking data, the drift of virtual images may be reduced. In one embodiment, the eye-tracking data could be used to determine a gaze axis and a target object in the displayed virtual images. The HMD may then move the target object towards a central axis. The HMD may also record data based on the gaze axis, central axis and target object to determine a user interface preference. The user interface preference could be used to adjust similar interactions with the HMD.

25 Claims, 11 Drawing Sheets

USER INTERFACE

BACKGROUND

Wearable systems can integrate various elements, such as miniaturized computers, input devices, sensors, detectors, image displays, wireless communication devices as well as image and audio processors, into a device that can be worn by a user. Such devices provide a mobile and lightweight solution to communicating, computing and interacting with one's environment. With the advance of technologies associated with wearable systems and miniaturized optical elements, it has become possible to consider wearable compact optical displays that augment the wearer's experience of the real world.

By placing an image display element close to the wearer's eye(s), an artificial image can be made to overlay the wearer's view of the real world. Such image display elements are incorporated into systems also referred to as "near-eye displays", "head-mounted displays" (HMDs) or "heads-up displays" (HUDs). Depending upon the size of the display element and the distance to the wearer's eye, the artificial image may fill or nearly fill the wearer's field of view.

SUMMARY

In a first aspect, a method is provided. The method includes displaying images on a display, the display having a central axis, determining a gaze axis with respect to the central axis, and determining a target object in the displayed images based on the gaze axis. The method further includes adjusting the displayed images on the display to move the target object towards the central axis.

In a second aspect, a method is provided. The method includes displaying images on a display, the display having a central axis. The method further includes determining a gaze axis with respect to the central axis, and determining a target object in the displayed images based on the gaze axis. The method further includes recording data based on the central axis, the gaze axis, the target object, and the displayed images. The method further includes adjusting the displayed images on the display based on the recorded data.

In a third aspect, a head-mounted display (HMD) is provided. The HMD includes a head-mounted support and an optical system attached to the head-mounted support. The optical system includes a display having a central axis and the display is configured to display images that are viewable from a viewing location. The HMD further includes an infrared light source configured to illuminate the viewing location with infrared light such that infrared light is reflected from the viewing location as reflected infrared light. The HMD further includes a camera configured to image the viewing location by collecting the reflected infrared light and a sensor configured to generate sensor data that relates to the motion of the HMD. The HMD further includes a computer configured to determine a gaze axis based on one or more images of the viewing location obtained by the camera, control the display to display images based on the sensor data, determine a target object in the displayed images based on the gaze axis, and control the display to move the target object towards the central axis.

In a fourth aspect, a non-transitory computer readable medium having stored instructions is provided. The instructions are executable by a computing device to cause the computing device to perform functions. The functions include: (i) controlling a display to display images, the display having a central axis; (ii) determining a gaze axis with respect to the central axis; (iii) determining a target object in the displayed images based on the gaze axis; and (iv) controlling the display to adjust the displayed images so as to move the target object towards the central axis.

In a fifth aspect, a method is provided. The method includes displaying images on a display of a head-mounted display (HMD). The displayed images are viewable at a viewing location and the display includes a central axis. The method further includes acquiring sensor data related to the motion of the HMD and controlling the display to display images based on the sensor data. The method also includes determining a gaze axis based on one or more images of the viewing location obtained by a camera and determining a target object in the displayed images based on the gaze axis. The method additionally includes controlling the display to move the target object towards the central axis.

DETAILED DESCRIPTION

Figure 1:
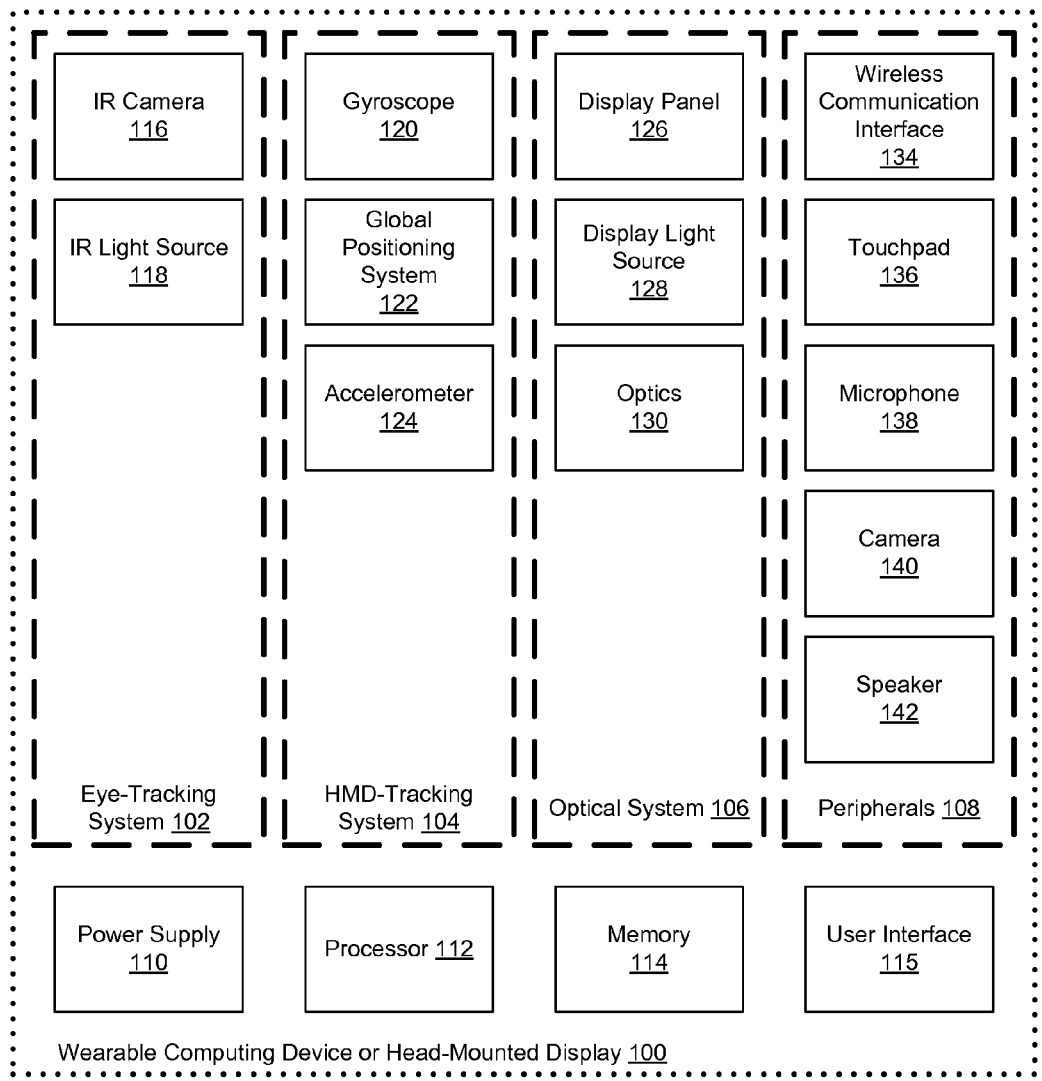
FIG. 1 is a schematic diagram of a wearable computing device, in accordance with an example embodiment.

In the following detailed description, reference is made to the accompanying figures, which form a part thereof. In the figures, similar symbols typically identify similar components, unless context dictates otherwise. The illustrative embodiments described in the detailed description and figures are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

1. Overview

A head-mounted display ("HMD") may enable its wearer to observe the wearer's real-world surroundings and also view a displayed image, such as a computer-generated image or virtual image. In some cases, the displayed image may overlay a portion of the wearer's field of view of the real world. Thus, while the wearer of the HMD is going about his or her daily activities, such as walking, driving, exercising, etc., the wearer may be able to see a displayed image generated by the HMD at the same time that the wearer is looking out at his or her real-world surroundings.

The displayed image might include, for example, graphics, text, and/or video. The content of the displayed image could relate to any number of contexts, including but not limited to the wearer's current environment, an activity in which the wearer is currently engaged, the biometric status of the wearer, and any audio, video, or textual communications that have been directed to the wearer. The images displayed by the HMD may also be part of an interactive user interface. For example, the HMD could be part of a wearable computing device. Thus, the images displayed by the HMD could include menus, selection boxes, navigation icons, or other user interface features that enable the wearer to invoke functions of the wearable computing device or otherwise interact with the wearable computing device.

The images displayed by the HMD could appear anywhere in the wearer's field of view. For example, the displayed image might occur at or near the center of the wearer's field of view, or the displayed image might be confined to the top, bottom, or a corner of the wearer's field of view. Alternatively, the displayed image might be at the periphery of or entirely outside of the wearer's normal field of view. For example, the displayed image might be positioned such that it is not visible when the wearer looks straight ahead but is visible when the wearer looks in a specific direction, such as up, down, or to one side. In addition, the displayed image might overlay only a small portion of the wearer's field of view, or the displayed image might fill most or all of the wearer's field of view. The displayed image could be displayed continuously or only at certain times (e.g., only when the wearer is engaged in certain activities).

The virtual images could be displayed based on the position and orientation of the HMD. For example, the HMD may include position and orientation sensors so that when the user moves his or her head, data regarding the position and orientation of the HMD can be received by a processor. The HMD may additionally include a display controllable by the processor, so when the user moves his or her head, the processor may adjust the displayed image on the display. In particular, the displayed image may move in the opposite direction of head movement to create the sensation of looking around a world with superimposed virtual images. In other words, the virtual images could be displayed to create the illusion that the graphical images are part of the real world.

However, HMD position and orientation sensors are unable to process information infinitely fast and are limited at least by the speed of the sensor hardware. Thus, when the HMD is in motion, some sensory data may be lost. Additionally, because of imperfections in the hardware and other factors, drifts, offsets, and other errors may be introduced into the sensor data. As a result, the processor may receive erroneous sensor data. For instance, when the sensor is at rest, the data it returns may cause the sensor appear as if it is in motion, at least slightly. Additional errors can occur when the sensor is in motion.

Sensor drift problems can be corrected for by, for example, software algorithms that may round or average data to reduce sensor error. These techniques can help resolve the drift problems when the sensor is at rest. However, these algorithms may not correct the problem when the sensor is in motion.

For instance, consider a HMD wearer traveling by train who is seated facing a side wall of the train. The HMD wearer may experience both a lateral shift while the train is in motion and also a gradual rotation change while the train rounds a corner. The position and orientation sensors of the HMD may measure these movements and may cause images to be displayed inappropriately. Drift errors may not be properly controlled in this situation by rounding or data averaging.

The below described methods, non-transitory computer readable media and apparatus may serve to reduce the effect of drift errors and unintentional HMD movement by utilizing eye-tracking information. The eye-tracking information could allow the determination of a gaze axis, which could be related to a target object in the images displayed by the HMD. Subsequently, the target object could be moved towards a central axis of the HMD.

In other words, the HMD may generally use HMD motion data to adjust virtual images on the display. For instance, as the HMD user walks around the real-world environment, virtual images could be presented to the wearer based upon the orientation of the HMD. However, when the system detects a target object selection from the eye-tracking system (e.g. the HMD wearer gazes at a specific object for a sufficient period of time), the HMD may act to move the target object to the central axis. In this manner, the determination of a gaze axis could act to override the HMD motion data and move or keep the target object near the central axis. Thus, errors due to imperfect sensor data and/or unintentional HMD movement could be reduced or eliminated.

Certain illustrative examples of a system and method for correcting sensor drift based on current and recorded eye gaze information are described below. It is to be understood, however, that other embodiments are possible and are implicitly considered within the context of the following example embodiments.

2. A Head-mounted Display Apparatus with Eye Tracking Functionality

FIG. 1 is a schematic diagram of a wearable computing device or a head-mounted display (HMD) 100 that may include several different components and subsystems. Components of the HMD 100 may include an eye-tracking system 102, a HMD-tracking system 104, an optical system 106, peripherals 108, a power supply 110, a processor 112, a memory 114, and a user interface 115. The eye-tracking system 102 may include hardware such as an infrared camera 116 and at least one infrared light source 118. The HMD-tracking system 104 may include a gyroscope 120, a global positioning system (GPS) 122, and an accelerometer 124. The optical system 106 may include, in one embodiment, a display panel 126, a display light source 128, and optics 130. The peripherals 108 may include, for example, a wireless communication interface 134, a touchpad 136, a microphone 138, a camera 140, and a speaker 142.

In an example embodiment, HMD 100 includes a see-through display. Thus, the wearer of HMD 100 may observe a portion of the real-world environment, i.e., in a particular field of view provided by the optical system 106. In the example embodiment, HMD 100 is operable to display virtual images that are superimposed on the field of view, for example, to provide an "augmented reality" experience. Some of the virtual images displayed by HMD 100 may be superimposed over particular objects in the field of view. HMD 100 may also display images that appear to hover within the field of view instead of being associated with particular objects in the field of view.

Components of the HMD 100 may be configured to work in an interconnected fashion with other components within or outside their respective systems. For instance, in an example embodiment, the infrared camera 116 may image one or both of the HMD wearer's eyes. The infrared camera 116 may deliver image information to the processor 112, which may access the memory 114 and make a determination regarding the direction of the HMD wearer's gaze, also termed a gaze axis. The processor 112 may further accept input from the GPS unit 122, the gyroscope 120, and/or the accelerometer 124 to determine the location and orientation of the HMD 100. Subsequently, the processor 112 may control the user interface 115 and the display panel 126 to display virtual images to the HMD wearer that may include context-specific information based on the HMD location and orientation as well as the HMD wearer's gaze axis.

HMD 100 could be configured as, for example, eyeglasses, goggles, a helmet, a hat, a visor, a headband, or in some other form that can be supported on or from the wearer's head. Further, HMD 100 may be configured to display images to both of the wearer's eyes, for example, using two see-through displays. Alternatively, HMD 100 may include only a single see-through display and may display images to only one of the wearer's eyes, either the left eye or the right eye. The HMD 100 may also represent an opaque display configured to display images to one or both of the wearer's eyes without a view of the real-world environment. Further, the HMD 100 could provide an opaque display for a first eye of the wearer as well as provide a view of the real-world environment for a second eye of the wearer.

A power supply 110 may provide power to various HMD components and could represent, for example, a rechargeable lithium-ion battery. Various other power supply materials and types known in the art are possible.

The function of the HMD 100 may be controlled by a processor 112 that executes instructions stored in a non-transitory computer readable medium, such as the memory 114. Thus, the processor 112 in combination with instructions stored in the memory 114 may function as a controller of HMD 100. As such, the processor 112 may control the user interface 115 to adjust the images displayed by HMD 100. The processor 112 may also control the wireless communication interface 134 and various other components of the HMD 100. The processor 112 may additionally represent a plurality of computing devices that may serve to control individual components or subsystems of the HMD 100 in a distributed fashion.

In addition to instructions that may be executed by the processor 112, the memory 114 may store data that may include a set of calibrated wearer eye pupil positions and a collection of past eye pupil positions. Thus, the memory 114 may function as a database of information related to gaze direction. Such information may be used by HMD 100 to anticipate where the user will look and determine what images are to be displayed to the wearer. Calibrated wearer eye pupil positions may include, for instance, information regarding the extents or range of the wearer's eye pupil movement (right/left and upwards/downwards) as well as wearer eye pupil positions that may relate to various reference axes.

Reference axes could represent, for example, an axis extending from a viewing location and through a target object or the apparent center of a field of view (i.e. a central axis that may project through a center point of the apparent display panel of the HMD). Other possibilities for reference axes exist. Thus, a reference axis may further represent a basis for determining dynamic gaze direction.

In addition, information may be stored in the memory 114 regarding possible control instructions that may be enacted using eye movements. For instance, two consecutive wearer eye blinks may represent a control instruction directing the HMD 100 to capture an image with a peripheral camera 140. Another possible embodiment may include a configuration such that specific eye movements may represent a control instruction. For example, a HMD wearer may unlock the user interface 115 with a series of predetermined eye movements.

Control instructions could be based on dwell-based selection of a target object. For instance, if a wearer fixates visually upon a particular virtual image or real-world object for longer than a predetermined time period, a control instruction may be generated to select the virtual image or real-world object as a target object. Many other control instructions are possible.

In addition to the aforementioned features, memory 114 could store various recorded data from previous HMD/user interactions. For instance, multiple images of a HMD wearer's eye(s) could be averaged to obtain an averaged eye gaze axis. This could lessen the effect of saccadic eye movements or saccades, in which the eye moves in a rapid and somewhat random manner around an eye gaze axis. These saccades help humans build up a mental image of a field of view with better resolution than if the eye remained static, and by averaging a number of eye images within a particular time period, an average gaze axis could be determined with less saccadic 'noise'.

Additionally, memory 114 could store recorded data regarding recent eye gaze axes for various application-based functions. For instance, the recent variance of the eye gaze axis could be coupled to scrolling images generated by the HMD 100. In this embodiment, if recent eye gaze axis variance is high, the images (e.g. text or other images) could scroll faster. If the eye gaze axis variance is low, the images may scroll slower or stop altogether. In this context, a lower variance in eye gaze axis could indicate the HMD wearer is concentrating on one particular gaze location, whereas a higher eye gaze axis variance means the opposite—the HMD wearer may be quickly scanning a document and desire a faster scrolling speed.

Depending on the content that is presented on the HMD display, the variance may differ depending on the axis along which it is measured. For example, the horizontal variance of a HMD wearer's eye gaze may be high while the vertical variance may be relatively low. This could indicate to the HMD 100 that the wearer is reading text. Accordingly, text scrolling/tracking could be adjusted in a different or more controlled fashion compared to 'non-reading' scrolling/panning/pagination situations.

The HMD 100 may include a user interface 115 for providing information to the wearer or receiving input from the wearer. The user interface 115 could be associated with, for example, the displayed virtual images, a touchpad, a keypad, buttons, a microphone, and/or other peripheral input devices. The processor 112 may control the functioning of the HMD 100 based on inputs received through the user interface 115. For example, the processor 112 may utilize user input from the user interface 115 to control how the HMD 100 displays images within a field of view or to determine what images the HMD 100 displays.

An eye-tracking system 102 may be included in the HMD 100. In an example embodiment, an eye-tracking system 102 may deliver information to the processor 112 regarding the eye position of a wearer of the HMD 100. The eye-tracking data could be used, for instance, to correct for sensor drift errors introduced by gaps in sensor data and/or sensor noise. In particular, the processor 112 could determine a target object in the displayed images based on information from the eye-tracking system 102. The processor 112 may then control the user interface 115 and the display panel 126 to adjust the target object and/or other displayed images in various ways. For instance, the target object could be held static on the display panel 126. Alternatively, the target object could be moved towards a central axis of the display panel 126.

An infrared camera 116 may be utilized by the eye-tracking system 102 to capture images of a viewing location associated with the HMD 100. Thus, the infrared camera 116 may image the eye of a HMD wearer that may be located at the viewing location. The viewing location may be illuminated by an infrared light source 118. The images could be either video images or still images. The images obtained by the infrared camera 116 regarding the HMD wearer's eye may help determine where the wearer is looking within the HMD field of view, for instance by allowing the processor 112 to ascertain the location of the HMD wearer's eye pupil. Analysis of the images obtained by the infrared camera 116 could be performed by the processor 112 in conjunction with the memory 114.

The imaging of the viewing location could occur continuously or at discrete times depending upon, for instance, user interactions with the user interface 115. The infrared camera 116 could be integrated into the optical system 106 or mounted on the HMD 100. Alternatively, the infrared camera could be positioned apart from the HMD 100 altogether. Furthermore, the infrared camera 116 could additionally represent a conventional visible light camera with sensing capabilities in the infrared wavelengths.

The infrared light source 118 could represent one or more infrared light-emitting diodes (LEDs) or infrared laser diodes that may illuminate a viewing location. One or both eyes of a wearer of the HMD 100 may be illuminated by the infrared light source 118. The infrared light source 118 may be positioned along an optical axis common to the infrared camera 116 and/or the infrared light source 118 may be positioned elsewhere. The infrared light source 118 may illuminate the viewing location continuously or may be turned on at discrete times. Additionally, when illuminated, the infrared light source 118 may be modulated at a particular frequency. Other types of modulation of the infrared light source 118 are possible.

The HMD-tracking system 104 could be configured to provide a HMD position and a HMD orientation to the processor 112. This position and orientation data may help determine a central axis to which a gaze axis is compared. For instance, the central axis may correspond to the orientation of the HMD.

The gyroscope 120 could be a microelectromechanical system (MEMS) gyroscope, a fiber optic gyroscope, or another type of gyroscope known in the art. The gyroscope 120 may be configured to provide orientation information to the processor 112. The GPS unit 122 could be a receiver that obtains clock and other signals from GPS satellites and may be configured to provide real-time location information to the processor 112. The HMD-tracking system 104 could further include an accelerometer 124 configured to provide motion input data to the processor 112.

The optical system 106 could represent components configured to provide virtual images to a viewing location. An example of optical system 106 is described in detail below with respect to FIG. 2.

Various peripheral devices 108 may be included in the HMD 100 and may serve to provide information to and from a wearer of the HMD 100. In one example, the HMD 100 may include a wireless communication interface 134 for wirelessly communicating with one or more devices directly or via a communication network. For example, wireless communication interface 134 could use 3G cellular communication, such as CDMA, EVDO, GSM/GPRS, or 4G cellular communication, such as WiMAX or LTE. Alternatively, wireless communication interface 134 could communicate with a wireless local area network (WLAN), for example, using WiFi. In some embodiments, wireless communication interface 134 could communicate directly with a device, for example, using an infrared link, Bluetooth, or ZigBee.

Although FIG. 1 shows various components of the HMD 100 (i.e., wireless communication interface 134, processor 112, memory 114, infrared camera 116, display panel 126, GPS 122, and user interface 115) as being integrated into HMD 100, one or more of these components could be physically separate from HMD 100. For example, the infrared camera 116 could be mounted on the wearer separate from HMD 100. Thus, the HMD 100 could be part of a wearable computing device in the form of separate devices that can be worn on or carried by the wearer. The separate components that make up the wearable computing device could be communicatively coupled together in either a wired or wireless fashion.

Figure 2:
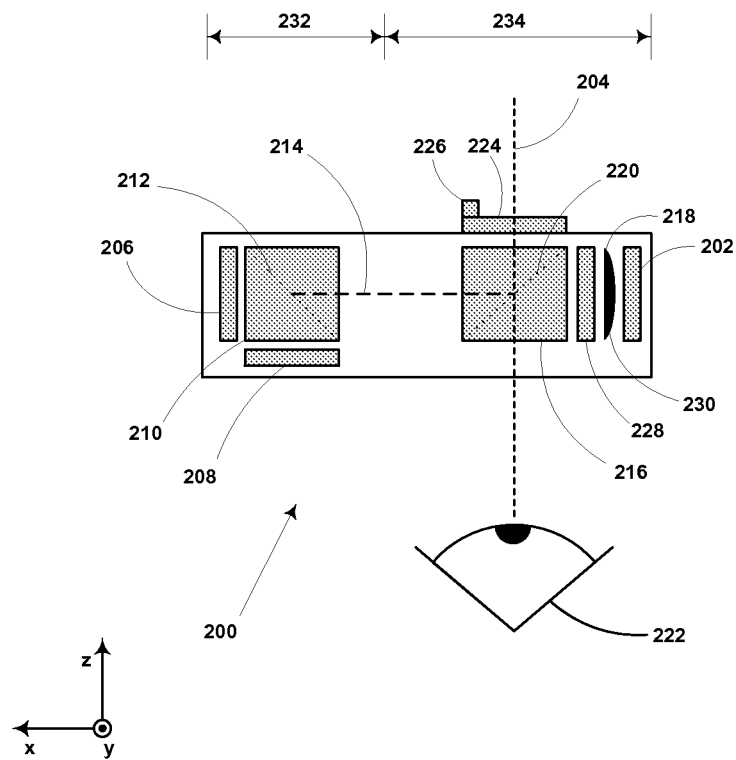
FIG. 2 is a top view of an optical system, in accordance with an example embodiment.

FIG. 2 illustrates a top view of an optical system 200 that is configured to display a virtual image superimposed upon a real-world scene viewable along a viewing axis 204. For clarity, a distal portion 232 and a proximal portion 234 represent optically-coupled portions of the optical system 200 that may or may not be physically separated. An example embodiment includes a display panel 206 that may be illuminated by a light source 208. Light emitted from the visible light source 208 is incident upon the distal beam splitter 210. The visible light source 208 may include one or more light-emitting diodes (LEDs) and/or laser diodes. The visible light source 208 may further include a linear polarizer that acts to pass one particular polarization to the rest of the optical system.

In an example embodiment, the distal beam splitter 210 is a polarizing beam splitter that reflects light depending upon the polarization of light incident upon the beam splitter. To illustrate, s-polarized light from the visible light source 208 may be preferentially reflected by a distal beam-splitting interface 212 towards the display panel 206. The display panel 206 in the example embodiment is a liquid crystal-on-silicon (LCOS) display. In an alternate embodiment in which the beam splitter coating at interface 212 is not a polarizing beam splitter, the display could be a digital light projector (DLP) micro-mirror display, or other type of reflective display panel. In either embodiment, the display panel 206 acts to spatially-modulate the incident light to generate a light pattern at an object plane in the display. Alternatively, the display panel 206 may be an emissive-type display such as an organic light-emitting diode (OLED) display, and in such a case, the beam splitter cube 210 is not needed.

In the example in which the display panel 206 is a LCOS display panel, the display panel 206 generates a light pattern with a polarization perpendicular to the polarization of light initially incident upon the panel. In this example embodiment, the display panel 206 converts incident s-polarized light into a light pattern with p-polarization. The generated light pattern from the display panel 206 is directed towards the distal beam splitter 210. The p-polarized light pattern passes through the distal beam splitter 210 and is directed along an optical axis 214 towards the proximal region of the optical system 200. In an example embodiment, the proximal beam splitter 216 is also a polarizing beam splitter. The light pattern is at least partially transmitted through the proximal beam splitter 216 to the image former 218. In an example embodiment, image former 218 includes a concave mirror 230 and a proximal quarter-wave plate 228. The light pattern passes through the proximal quarter-wave plate 228 and is reflected by the concave mirror 230.

The reflected light pattern passes back through proximal quarter-wave plate 228. Through the interactions with the proximal quarter-wave plate 228 and the concave mirror 230, the light patterns are converted to the s-polarization and are formed into a viewable image. This viewable image is incident upon the proximal beam splitter 216 and the viewable image is reflected from proximal beam splitting interface 220 towards a viewing location 222 along a viewing axis 204. A real-world scene is viewable through a viewing window 224. The viewing window 224 may include a linear polarizer in order to reduce stray light within the optical system. Light from the viewing window 224 is at least partially transmitted through the proximal beam splitter 216. Thus, both a virtual image and a real-world image are viewable to the viewing location 222 through the proximal beam splitter 216.

Although FIG. 2 depicts the distal portion 232 of the optical system housing as to the left of the proximal portion 234 of the optical system housing when viewed from above, it is understood that other embodiments are possible to physically realize the optical system 200, including the distal portion 232 being configured to be to the right, below and above with respect to the proximal portion 234. Further, although an example embodiment describes an image former 218 as comprising a concave mirror 230, it is understood by those skilled in the art that the image former 218 may comprise a different optical element, such as an optical lens or a diffractive optic element.

In one embodiment, the proximal beam splitter 216, the distal beam splitter 210, and other components of optical system 200 are made of glass. Alternatively, some or all of such optical components may be partially or entirely plastic, which can also serve to reduce the weight of optical system 200. A suitable plastic material is Zeonex® E48R cyclo olefin optical grade polymer which is available from Zeon Chemicals L.P., Louisville, Ky. Another suitable plastic material is polymethyl methacrylate (PMMA).

An example embodiment may include an infrared light source 226 that is configured to illuminate the viewing location 222. Although FIG. 2 depicts the infrared light source 226 as adjacent to viewing window 224, those skilled in the art will understand that the infrared light source 226 could be located elsewhere, such as on the side of the proximal beam splitter 216 that is adjacent to the viewing location 222 or in the distal portion 232 of the optical system 200. The infrared light source 226 may represent, for example, one or more infrared light-emitting diodes (LEDs). Infrared LEDs with a small size may be implemented, such as the Vishay Technology TSML 1000 product.

Those skilled in the art will understand that, for best eye-tracking accuracy, it may be advantageous to obtain infrared images of the eye pupil using light sources that illuminate the eye from positions off-axis and/or on-axis with respect to the viewing axis 204. Therefore, the infrared light source 226 may include one or more LEDs located at different locations in, and/or separate from, the optical system 200.

Infrared light generated from the infrared light source 226 is configured to be incident upon the viewing location 222. Thus, the wearer's eye pupil may be illuminated with the infrared light. The infrared light may be reflected from the wearer's eye back along the viewing axis 204 towards the proximal beam splitter 216. A portion of the reflected infrared light may be reflected from the beam splitting interface 220 towards the image former 218.

In order to transmit infrared light to an infrared camera 202, the image former 218 may include a dichroic thin film configured to selectively reflect or transmit incident light depending upon the wavelength of the incident light. For instance, the dichroic thin film may be configured to pass infrared light while reflecting visible light. In an example embodiment, the visible light pattern generated by the display panel 206 may be reflected by the concave mirror 230 and the visible light pattern may be formed into a viewable image. The infrared light may thus be preferably transmitted through the concave mirror 230 to the infrared camera 202. Dichroic thin film coatings are available commercially from companies such as JML Optical Industries and Precision Glass & Optics (PG&O) and comprise multiple layers of dielectric and/or metal films. These dichroic coatings are also called 'cold mirrors'.

In an example embodiment, a small aperture may be introduced into the image former 218, which may be realized by a pinhole in the center of the concave mirror 230. In this example embodiment, most of the visible and infrared light is reflected off of and is formed by the image former 218 into an image viewable by the HMD wearer. Some of the visible and infrared light passes through the aperture and is incident upon the infrared camera 202. The infrared camera 202 may selectively filter and detect the infrared light from the combination of visible and infrared light to obtain information regarding the wearer's eye pupil location. Alternatively and/or additionally, the infrared light source 226 may be modulated with respect to a clock signal of a lock-in amplifier or phase-locked loop in order that the infrared light signal is transduced efficiently. Also, the visible light source 208 may be modulated and infrared light detection could be performed when the visible light source 208 is off, for example. Reflected infrared light may also be collected from off-axis angles, and thus the infrared camera may also be located elsewhere on optical system 200 or located separately from optical system 200. Those with skill in the art will understand that there are other variations of transducing an infrared light signal mixed with a visible light signal with an infrared camera and that those variations are included implicitly in this specification.

Figure 3A:
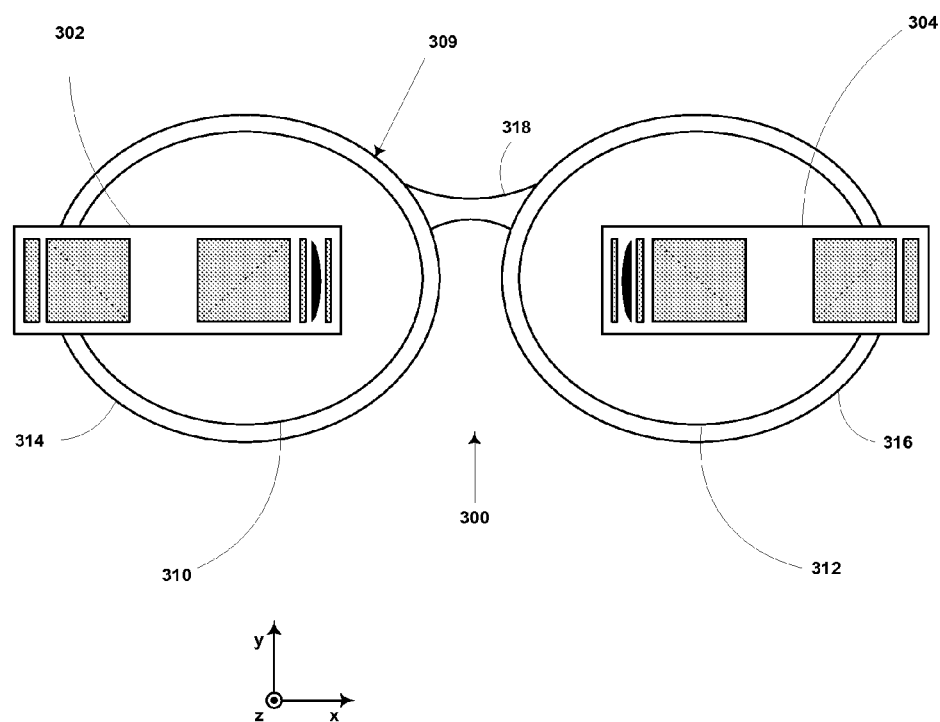
FIG. 3A is a front view of a head-mounted display, in accordance with an example embodiment.
Figure 3B:
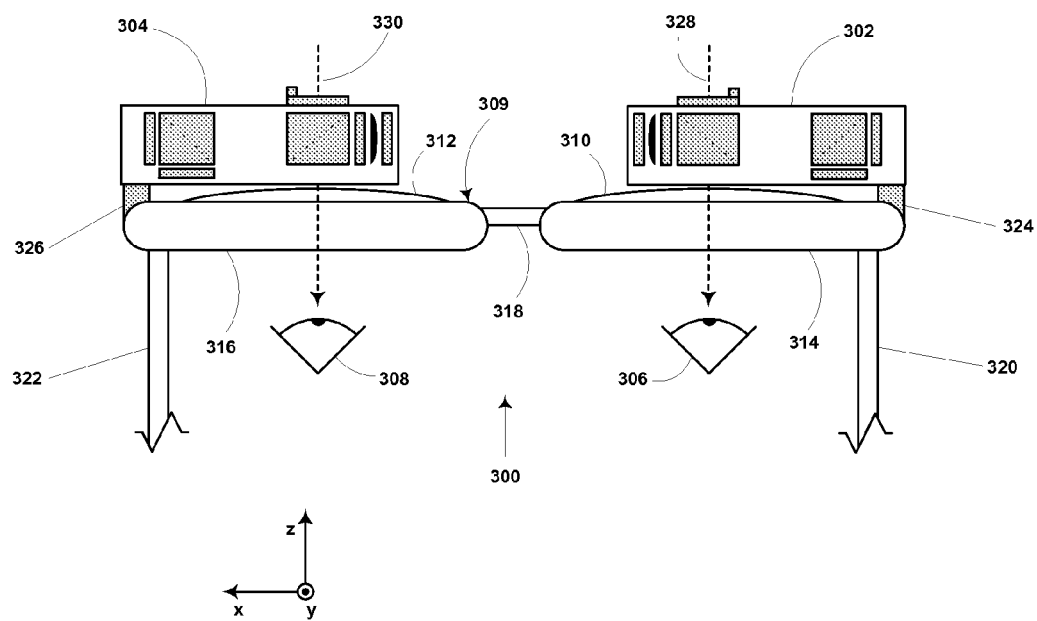
FIG. 3B is a top view of the head-mounted display of FIG. 3A, in accordance with an example embodiment.
Figure 3C:
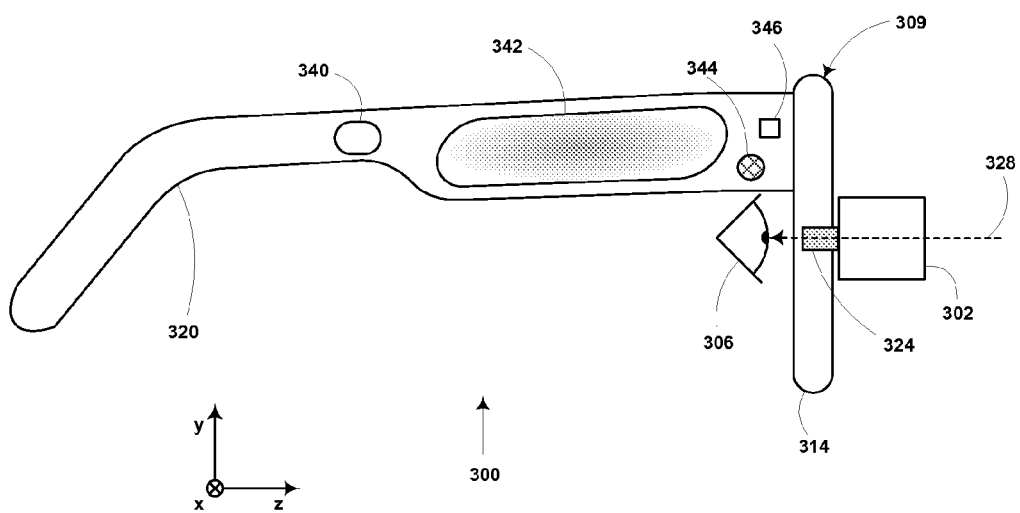
FIG. 3C is a side view of the head-mounted display of FIG. 3A and FIG. 3B, in accordance with an example embodiment.

FIG. 3A presents a front view of a head-mounted display (HMD) 300 in an example embodiment that includes a head-mounted support 309. FIGS. 3B and 3C present the top and side views, respectively, of the HMD in FIG. 3A. Although this example embodiment is provided in an eyeglasses format, it will be understood that wearable systems and HMDs may take other forms, such as hats, goggles, masks, headbands and helmets. The head-mounted support 309 includes lens frames 314 and 316, a center frame support 318, lens elements 310 and 312, and extending side-arms 320 and 322. The center frame support 318 and side-arms 320 and 322 are configured to secure the head-mounted support 309 to the wearer's head via the wearer's nose and ears, respectively. Each of the frame elements 314, 316, and 318 and the extending side-arms 320 and 322 may be formed of a solid structure of plastic or metal, or may be formed of a hollow structure of similar material so as to allow wiring and component interconnects to be internally routed through the head-mounted support 309. Alternatively or additionally, head-mounted support 309 may support external wiring. Lens elements 310 and 312 are at least partially transparent so as to allow the wearer to look through them. In particular, the wearer's left eye 308 may look through left lens 312 and the wearer's right eye 306 may look through right lens 310. Optical systems 302 and 304, which may be configured as shown in FIG. 2, may be positioned in front of lenses 310 and 312, respectively, as shown in FIGS. 3A, 3B, and 3C. Optical systems 302 and 304 may be attached to the head-mounted support 309 using support mounts 324 and 326, respectively. Furthermore, optical systems 302 and 304 may be integrated partially or completely into lens elements 310 and 312, respectively.

Although this example includes an optical system for each of the wearer's eyes, it is to be understood that a HMD might include an optical system for only one of the wearer's eyes (either left eye 308 or right eye 306). As described in FIG. 2, the HMD wearer may simultaneously observe from optical systems 302 and 304 a real-world image with an overlaid virtual image. The HMD 300 may include various elements such as a processor 340, a touchpad 342, a microphone 344, and a button 346. The computer 340 may use data from, among other sources, various sensors and cameras to determine the virtual image that should be displayed to the user. In an example embodiment, as described earlier, an infrared light source or sources may illuminate the viewing position(s) 308 and 306, i.e. the wearer's eye(s), and the reflected infrared light may be collected with an infrared camera.

Those skilled in the art would understand that other user input devices, user output devices, wireless communication devices, sensors, and cameras may be reasonably included in such a wearable computing system.

Figure 4A:
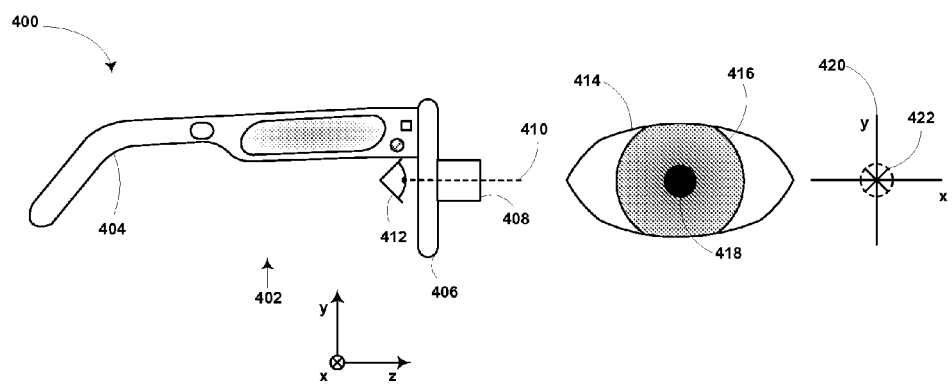
FIG. 4A is a side view of a head-mounted display with a forward gaze axis, in accordance with an example embodiment.
Figure 4B:
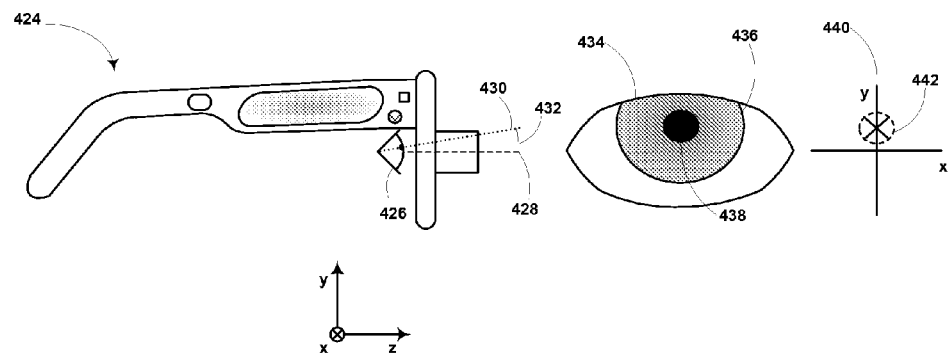
FIG. 4B is a side view of the head-mounted display of FIG. 4A with an upward gaze axis, in accordance with an example embodiment.

FIGS. 4A and 4B depict side and front views of an eye as well as schematic drawings of pupil location information under different conditions. One way to determine a gaze axis of an eye is to ascertain the position of an eye pupil with respect to a reference point. In an example embodiment that tracks eye pupil position, infrared light is reflected off of a person's eye. The reflected light may be imaged with an infrared camera. Upon imaging of the eye, image processing can be conducted with a processor 112 in order to determine, for instance, the extents and centroid location of the person's pupil. Other known means and methods of eye-tracking, including the use of visible light illumination and/or other imaging techniques are possible.

In an embodiment 400, a person may be looking directly forward as depicted in FIG. 4A. The eye 412 is open and the pupil 418 is located along a central axis 410. After image processing, which may include edge detection, the position of the pupil may be determined to be at pupil location 422. In this example, the processor 112 may subsequently determine that the gaze axis, based on the pupil location 422, coincides with a central axis 410. Virtual image display position and movement may be adjusted due to the determined pupil location 422. For instance, the processor 112 may adjust a tracking rate to zero when a gaze axis and the central axis are equivalent or nearly equivalent. This may allow a user to slowly read critical text or closely examine a virtual image, for example.

In an example embodiment 424, as illustrated in FIG. 4B, a person may be looking upwards with respect to a central axis 428. The eye 434 is open and the pupil location is generally higher than a reference point 440. In this situation, imaging the person's pupil 438 with infrared light may result in a determined pupil position 442. The processor 112 may determine that the gaze axis 430 is inclined above the central axis 428. The angle difference 432 may represent the absolute difference in angle between the central axis 428 and the gaze axis 430. The processor 112 may calculate the angle difference 432 and, based on the angle difference 432, adjust a tracking rate. For instance, a large angle difference 432 could represent an adjustment in tracking rate such that the tracking rate is higher, for instance to scroll a virtual image across a field of view at a faster rate. In other embodiments, the processor 112 may calculate the angle difference 432 and move a target object in the displayed images in order to minimize the angle difference 432. In other words, HMD display may be controlled such that the target object is moved toward the center of the HMD display.

Other embodiments could include the use of different eye gaze determination techniques. For instance, instead of using the eye pupil to determine gaze axis, it is possible to track eye motions using the boundary between the sclera and iris (the boundary is labelled as 416 and 436 in FIGS. 4A and 4B, respectively). For the purposes of determining an eye gaze axis, finding the centroid of the sclera/iris boundary (also called the limbus) may be equivalent to finding the centroid of a pupil.

Other possibilities for eye-tracking exist that may determine different reference points on the eye and may be implemented within the context of this invention. For instance, instead of ascertaining the pupil centroid to determine the gaze axis, position data from multiple glint reflections on the eye may be used in addition to or in lieu of information about the pupil position to determine the gaze axis.

3. Method for Adjusting Virtual Images on a Display Based on a Gaze Axis and a Central Axis of the Display.

Figure 5:
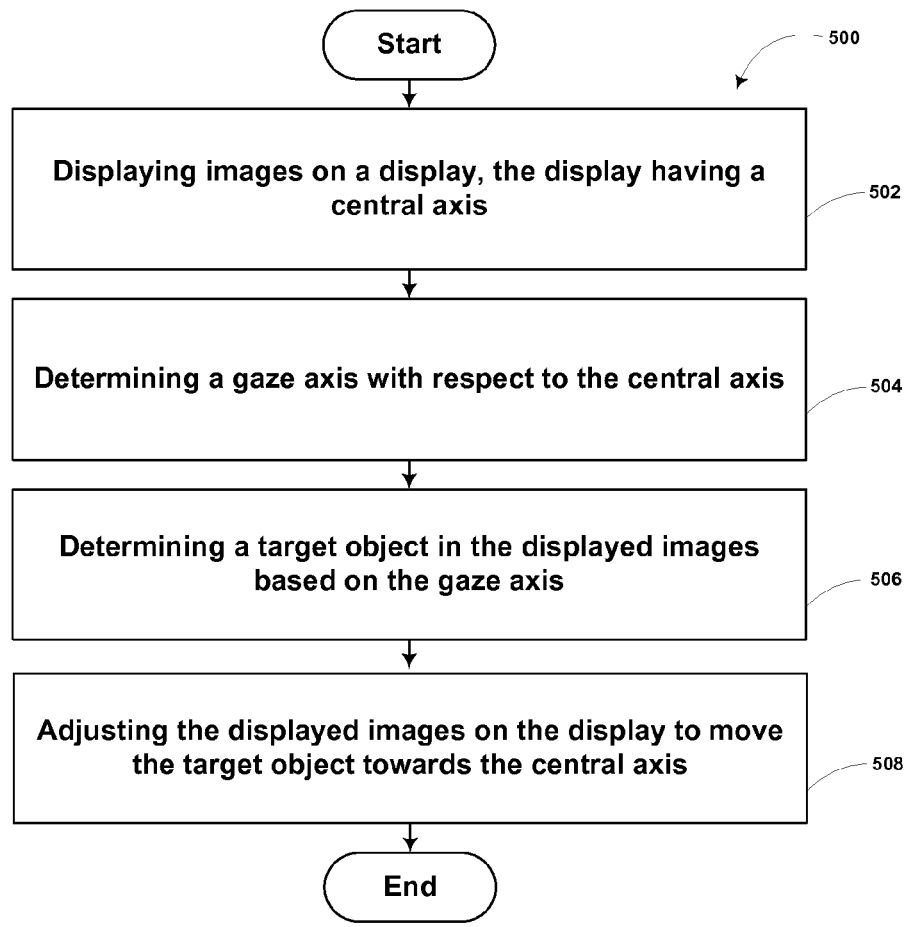
FIG. 5 is a flowchart of a method, in accordance with an example embodiment.

A method 500 is provided for adjusting displayed images on a display to move the target object closer to the central axis. Method 500 could be performed using a HMD that could be configured as shown in any of FIGS. 1 through 3C, or configured in some other way. FIG. 5 illustrates the steps in an example method, however, it is understood that in other embodiments, the steps may appear in different order and steps may be added or subtracted.

Step 502 includes displaying images on a display. The display may have a central axis that could be considered a line passing through the center of the display, normal to the display itself. In alternate embodiments, the central axis may pass through other locations on the display that may not be at the center of the display, for instance if the display is not symmetric.

As discussed above, the display may present a wide variety of virtual images to a user including text, shapes, pictures, etc. These virtual images may allow the HMD wearer to experience an augmented reality.

Step 504 includes determining a gaze axis with respect to the central axis. The determination of a gaze axis could be performed through eye-tracking. For example, an eye-tracking system 102 could be used to image the eye of an HMD wearer to determine the position of his or her eye pupil and therefore determine a gaze axis, such as illustrated in FIGS. 4A and 4B.

Step 506 includes determining a target object in the displayed images based on the gaze axis. After determining a gaze axis, the processor 112 could determine that the wearer is gazing at a specific target object among the set of displayed images. This target object could be any virtual image from the images being displayed on the display. For example, a wearer may be viewing lines of virtual text and may gaze fixedly at a particular word or phrase. In turn, the word or phrase could be determined to be a target object.

Step 508 includes adjusting the displayed images on the display to move the target object towards the central axis. This step could include moving a whole set of displayed images (including the target object) toward the central axis. For instance, following the previous example embodiment where a specific word or phrase is the target object, the entire formatted body of text may be moved towards the central axis.

Alternatively, only the target object may move towards the central axis. For instance, if a virtual image representing a specific icon from a set of icons is determined to be the target object, the processor 112 may move only the target object icon toward the central axis of the display. Other movements are possible as well, including dynamic reformatting of text and other virtual images while moving a target object towards the central axis.

The rate at which the target object is moved, or the tracking rate, may be based on the angle between the gaze axis and the target axis, among other factors. For instance, if the HMD wearer is gazing at a target object near the edge of the field of view of the HMD (thus, the angle difference is large), the target object may be moved at a tracking rate that is relatively fast. Conversely, if the target object is only slightly separated from the central axis, the tracking rate may be slow.

Figure 7A:
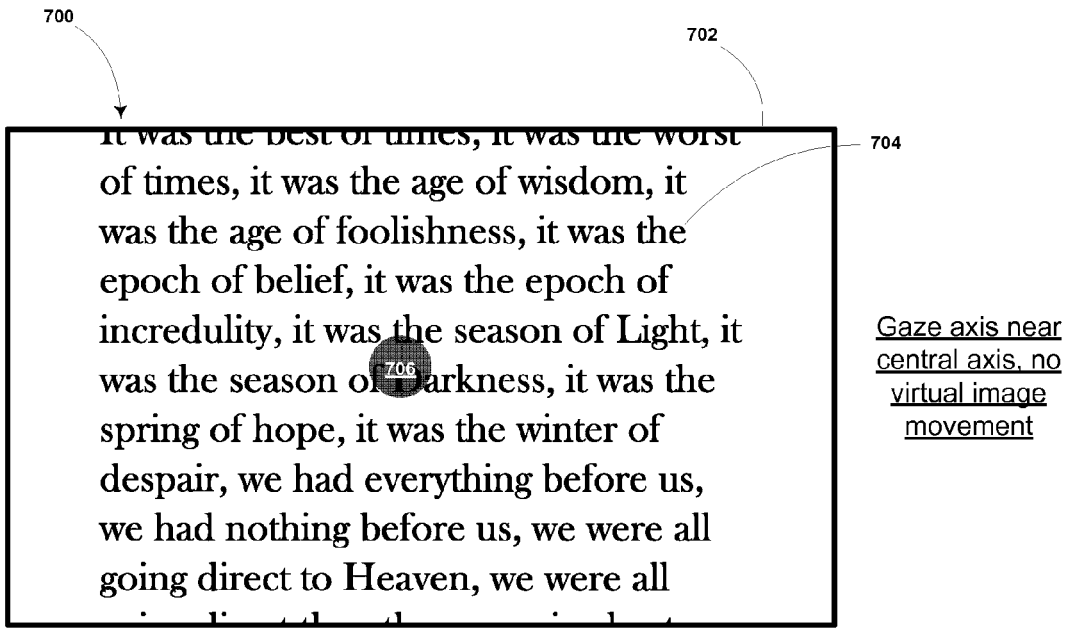
FIG. 7A shows a field of view of an HMD, in accordance with an example embodiment.
Figure 7B:
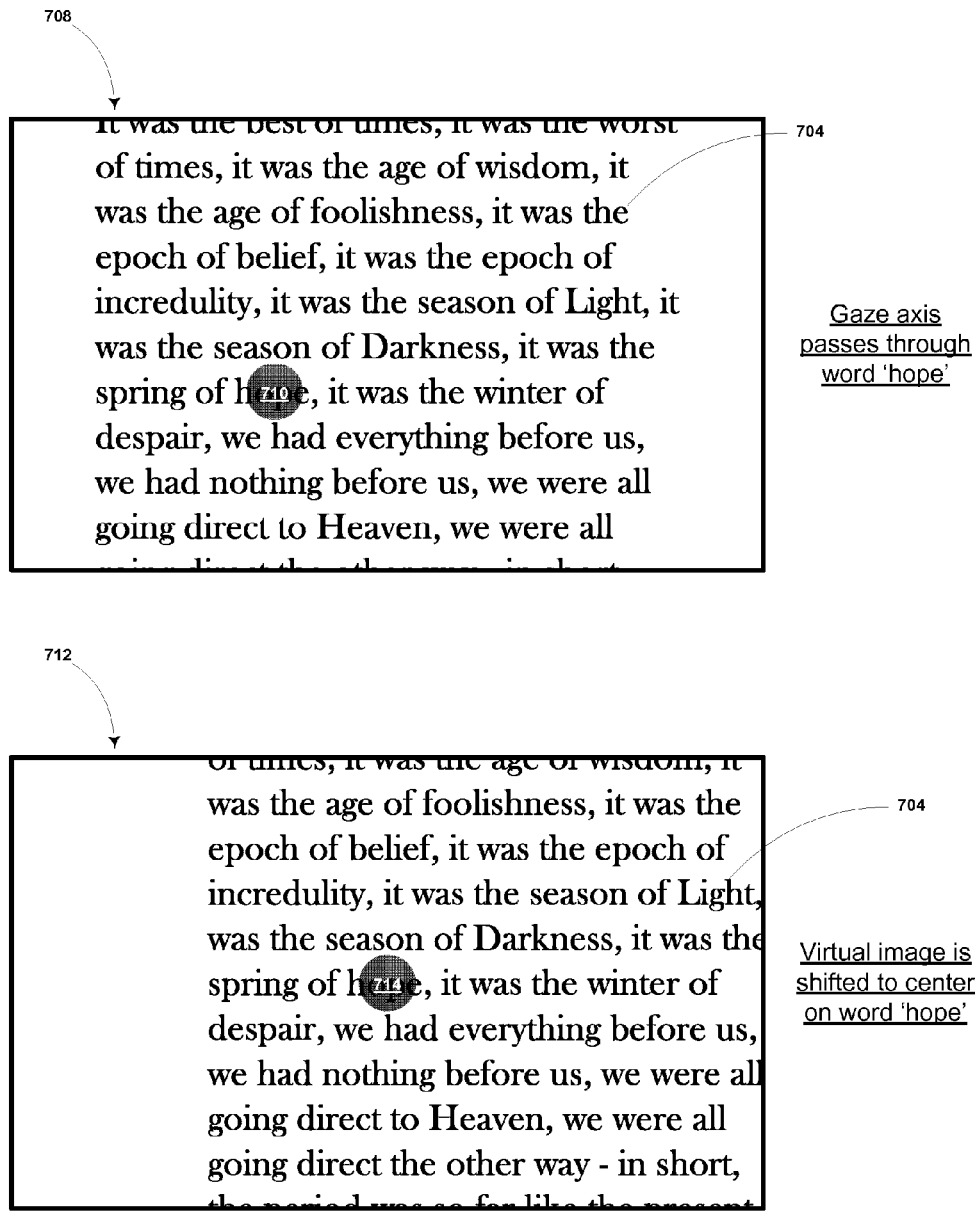
FIG. 7B shows two fields of view of an HMD, in accordance with an example embodiment.

An example of method 500 is illustrated in FIGS. 7A and 7B. FIG. 7A shows a HMD field of view 700 in which virtual text 704 is being presented to the HMD wearer. An eye-tracking system 102 could determine that an eye gaze axis may pass through the display 702 at a central eye gaze point 706. The target object could be determined to be the word, 'of.' Since the target object is near the center of the display, the gaze axis and central axis are aligned or nearly so. Thus, the processor 112 may determine that the wearer is gazing at the center of the screen and no virtual image movement may occur.

In FIG. 7B, a related field of view 708 may be presented to the HMD wearer. The HMD wearer is determined to have a gaze point 710 within a set of virtual text 704. In this example, the eye-tracking system 102 and processor 112 may determine that the wearer is gazing at the word, 'hope' and determine that word to be the target object. Thus, the virtual images may be adjusted so that the word 'hope' is moved toward the central axis. Another field of view 712 may be presented to the HMD wearer where the set of virtual text 704 has been moved to the right and up such that the target object (in this example, the word 'hope') is located along the central axis of the display.

Figure 6:
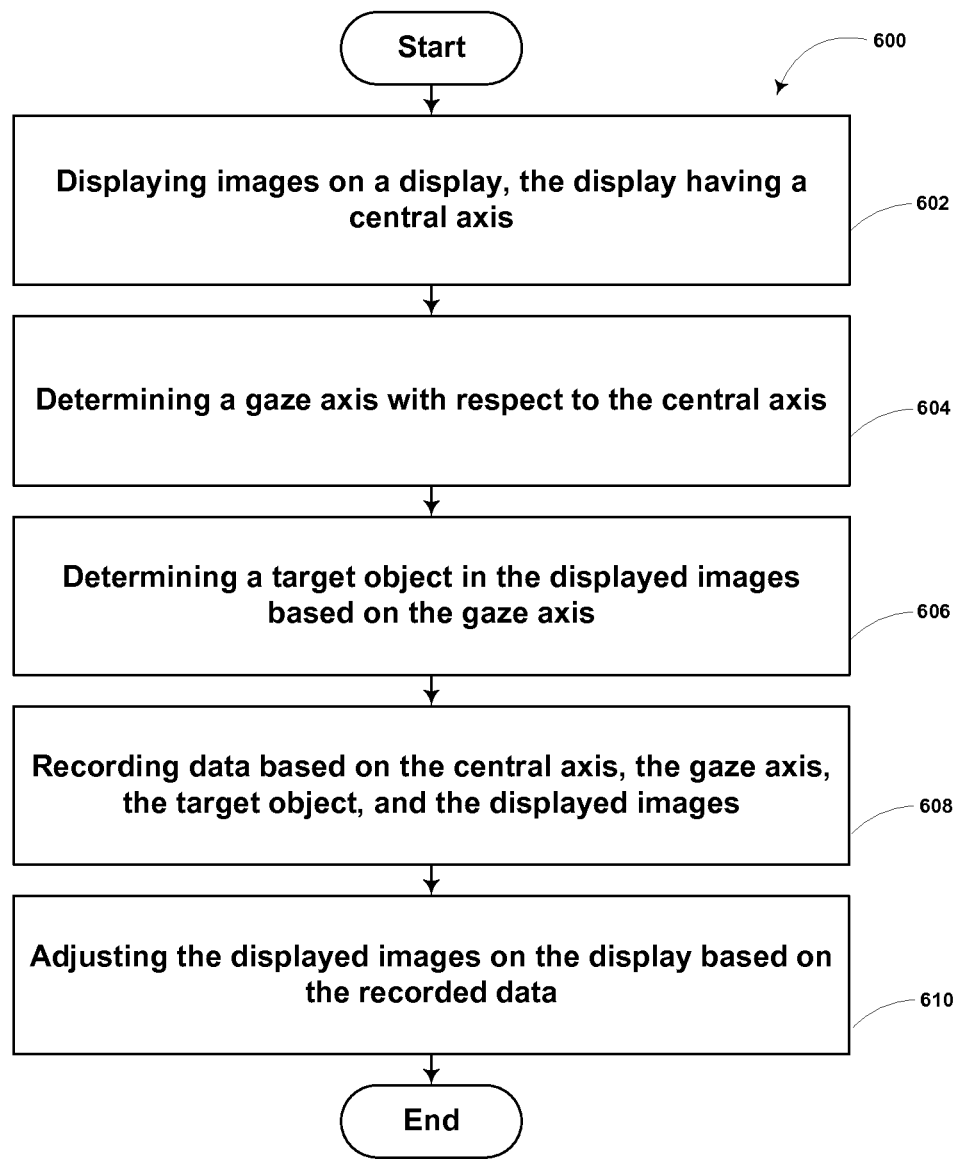
FIG. 6 is a flowchart of a method, in accordance with an example embodiment.

4. Method for Recording Data Based on a Gaze Axis, a Target Object and a Central Axis of a Display and Adjusting the Displayed Images on the Display Based on the Recorded Data A method 600 is provided for recording data based on the central axis, gaze axis, and target object and adjusting displayed images on a display to move the target object closer to the central axis. Method 600 could be performed using a HMD that could be configured as shown in any of FIGS. 1 through 3C, or configured in some other way. FIG. 6 illustrates the steps in an example method, however, it is understood that in other embodiments, the steps may appear in different order and steps may be added or subtracted.

In a first step 602, images are displayed on a display. The display may have a central axis that could be represented by a line that passes through the display at a normal incidence. The central axis may pass through other locations on the display that may not be at the center of the display, for instance if the display is not symmetric.

In a second step 604, a gaze axis may be determined with respect to the central axis. For example, a means for eye-tracking, such as eye-tracking system 102, may be used to acquire images of an HMD wearer's eye. The images could be used by processor 112 in order to determine information regarding the wearer's eye position, for instance, a centroid of a wearer's pupil and from this information further determine a gaze axis.

In a third step 606, a target object may be determined based on the gaze axis. For example, a processor 112 may determine that a particular gaze axis may be associated with a target object from among the displayed virtual images on the display. In one embodiment, the gaze axis may pass through a displayed virtual image that may be determined to be the target object. In other embodiments, target objects may be determined from the gaze axis even if the gaze axis does not intersect a corresponding virtual image. For instance, an HMD wearer may gaze fixedly at a particular virtual image on the display. Correspondingly, the processor 112 may determine a target object not spatially related to the virtual image of interest.

In a fourth step 608, data may be recorded based on the central axis, the gaze axis, the target object, and the displayed images. For instance, data regarding the central axis, the gaze axis of an HMD wearer, the target object, and the displayed images may be stored in memory 114. The data could be recorded in a continuous fashion, or only be recorded when specific tasks are being performed. Alternatively or additionally, data could be recorded upon user request through the user interface 115 or during other HMD operations.

In a fifth step 610, the displayed images may be adjusted on the display based on the recorded data. In one example embodiment, data may be recorded during normal wearer interaction with the HMD. The data may include information, for instance regarding the HMD wearer's average reading speed, that could thereafter be used to adjust the virtual images displayed on the screen when the HMD wearer is reading text. For example, the rate of automated text scrolling could be controlled by prerecorded data regarding the wearer's average reading speed. The HMD could obtain data to determine user preferences that may encompass a broad range of various HMD user interactions and functions.

Other examples of how such recorded data could be used are possible. For example, the recorded data could be used for HMD calibration. Due to variations in interocular spacing and facial features between users, information from the eye-tracking system may vary slightly from one HMD wearer to the next, even when the users are performing the same actions. Thus, eye gaze determinations may also vary between individuals. A processor 112 could analyze the data stored in the memory 114 to match a user eye gaze input to an intended user input. Displayed images on the display could depend at least on the results of the recorded data and corresponding user customizations. By recording data regarding eye-tracking interactions with the HMD, the need for calibration and customization for individual users may be reduced.

5. Non-transitory Computer Readable Medium for Sensor Drift Correction

Some or all of the functions described above and illustrated in FIGS. 5, 6, 7A and 7B may be performed by a computing device in response to the execution of instructions stored in a non-transitory computer readable medium. The non-transitory computer readable medium could be, for example, a random access memory (RAM), a read-only memory (ROM), a flash memory, a cache memory, one or more magnetically encoded discs, one or more optically encoded discs, or any other form of non-transitory data storage. The non-transitory computer readable medium could also be distributed among multiple data storage elements, which could be remotely located from each other. The computing device that executes the stored instructions could be a wearable computing device, such as a wearable computing device 100 illustrated in FIG. 1. Alternatively, the computing device that executes the stored instructions could be another computing device, such as a server in a server network.

With reference to FIG. 1, the non-transitory computer readable medium, which may correspond to memory 114, may store instructions executable by the processor 112 to perform various functions. For instance, upon receiving gaze axis information from the eye-tracking system 102, the processor 112 may be instructed to control the display panel 126 to adjust the displayed images based on, for instance, the gaze axis and the central axis. In another embodiment, data could be recorded based on the gaze axis, central axis and target object in order to adjust the target object on the display or determine a user interface preference. The user interface preference could be used to adjust similar interactions with the HMD in the future. Those skilled in the art will understand that other sub-functions or functions may be reasonably included to instruct a processor to adjust a virtual image on a display based upon eye-tracking and other sensor data.

Figure 8:
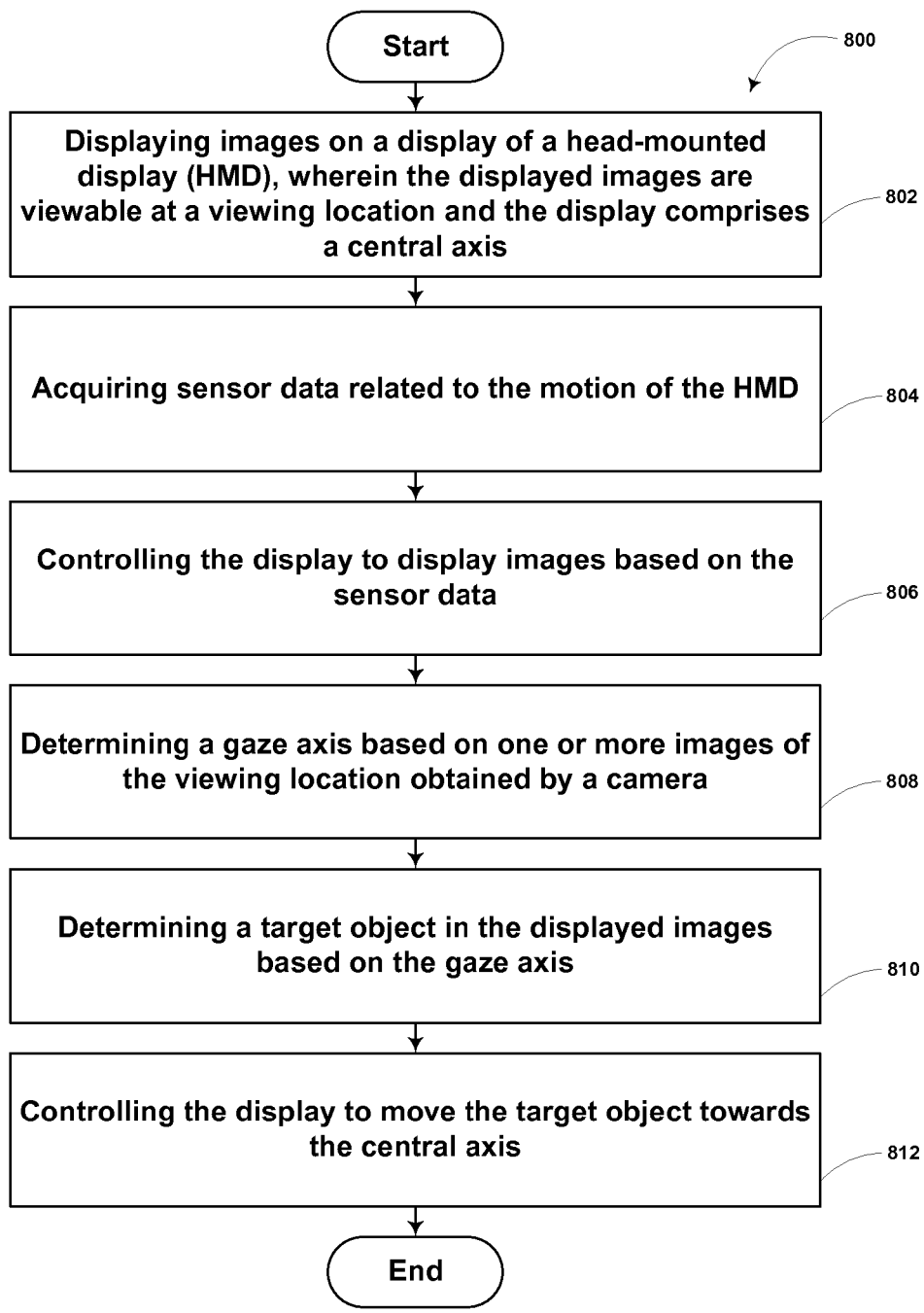
FIG. 8 is a flowchart of a method, in accordance with an example embodiment.

6. Method for Displaying Images in a HMD Based on the Movement of the HMD and Eye-tracking Data A method 800 is provided for displaying images on a display of a head-mounted display (HMD) based on the movement of the HMD and eye-tracking data of the HMD wearer. Method 800 could be performed using a HMD that could be configured as shown in any of FIGS. 1 through 3C, or configured in some other way. FIG. 8 illustrates the steps in an example method, however, it is understood that in other embodiments, the steps may appear in different order and steps may be added or subtracted.

Method step 802 includes displaying images on a display of a HMD. In this embodiment, the displayed images are viewable at a viewing location and the HMD display has a central axis. The viewing location could be, for instance, the location of an eye (or both eyes) of the HMD wearer. Similar to aforementioned embodiments, the central axis could be an axis protruding normally from the center of the HMD display.

Method step 804 includes acquiring sensor data related to the motion of the HMD. The sensor data could be generated by, for instance, the accelerometer 124 and/or gyroscope 120. The sensor data could include information such as the angle and azimuth of the HMD, which may correspond to the angle and azimuth of the central axis. Further, the sensor data could include information regarding the position of the HMD, such as may be acquired by the GPS 122. Other types of sensor data, such as HMD velocity and acceleration information, are possible and may be reasonably applied using the example embodiment.

Method step 806 includes controlling the display to display images based on the sensor data. In the example embodiment, the HMD could provide a graphical user interface in response to a movement of the HMD. The graphical user interface could be configured to be displayed in response to any HMD movement, or alternately, in response to a predetermined HMD movement. Thus, processor 112 could be configured to acquire sensor data. In response to an appropriate sensor data input, the processor 112 could control the optical system 106 to display images associated with a graphical user interface. For instance, if the HMD user moves his or her head upwards, the graphical user interface could be provided.

Further, while the graphical user interface is provided by the HMD, the user may view virtual images that could appear overlaid upon the real world environment. These virtual images could be substantially anchored to real world objects and/or reference points. Alternatively or additionally, some or all of the virtual images could stay substantially fixed with respect to, in one example, the azimuth (rotation angle within the horizontal plane) of the HMD. Thus, the HMD wearer could view different aspects of the graphical user interface by rotating his or her head and/or body.

The method step 808 includes determining a gaze axis based on one or more images of the viewing location using a camera. In this step, as described in above embodiments, an infrared camera could work together with an infrared light source or sources to image the HMD wearer's eye(s). The images may be captured in an effort to ascertain a gaze direction or gaze axis of the HMD wearer. The gaze direction/axis may relate to the direction in which the user is looking.

In method step 810, a target object may be determined within the displayed images based on the gaze axis. Thus, using information obtained from method step 808, the processor 112 could be used to determine a particular target object from the set of currently displayed images. For example, a target object may be determined based on the point of intersection of the gaze direction and the display panel 126.

Method step 812 includes controlling the display to move the target object towards the central axis. Within the context of this method, the user may be interacting within an established graphical user interface that could overlay his or her view of the real world environment. By gazing at a particular element within the graphical user interface could select it from the set of currently displayed images. The particular element could thus be selected to become the target object. Target object selection could be performed by gazing at the element for a predetermined period of time. The target object may then be moved towards the central axis of the HMD. This movement of the target object could allow the HMD wearer to, for instance, read a passage of text more easily or concentrate on a particular area of interest on an image. Additionally, as the centering action in method step 812 could be independent of HMD movement, the method could be useful to reduce the effect of noise on drift in the sensor data, as well as unintentional movement of the HMD. In effect, commands to move the displayed images based on the HMD motion data can be 'overridden' when eye-tracking data may indicate a target object. In this manner, display of images could be essentially decoupled from HMD motion, which may reduce or eliminate the effect of unwanted motion sensor drift and HMD movement.

Those skilled in the art will understand that there are other possible ways of using HMD movement data and eye-tracking data to center target objects on a display of a HMD, and the aforementioned example embodiment is not meant to preclude any other such examples.

CONCLUSION

The above detailed description describes various features and functions of the disclosed systems, devices, and methods with reference to the accompanying figures. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
    displaying images on a display, the display having a central axis;
    determining a gaze axis with respect to the central axis;
    determining a target object in the displayed images based on the gaze axis; and
    adjusting the displayed images on the display to move the target object towards the central axis, wherein adjusting the displayed images on the display comprises moving the target object at a tracking rate and adjusting the tracking rate based on a difference between the gaze axis and the central axis.

2. The method of claim 1, wherein determining the gaze axis comprises:
    obtaining an eye pupil image;
    determining the gaze axis from the eye pupil image.

3. The method of claim 1, wherein determining the gaze axis comprises:

obtaining a plurality of eye pupil images; and determining the gaze axis from the plurality of eye pupil images.

4. The method of claim 1, wherein adjusting the displayed images on the display to move the target object towards the central axis comprises:

moving a set of displayed images towards the central axis, wherein the set of displayed images comprises the target object.

5. A head-mounted display (HMD), comprising:

a head-mounted support;

an optical system attached to the head-mounted support, wherein the optical system comprises a display having a central axis, wherein the display is configured to display images that are viewable from a viewing location;

an infrared light source configured to illuminate the viewing location with infrared light such that infrared light is reflected from the viewing location as reflected infrared light;

a camera configured to image the viewing location by collecting the reflected infrared light;

a sensor configured to generate sensor data that relates to motion of the HMD; and a computer configured to determine a gaze axis based on one or more images of the viewing location obtained by the camera, control the display to display images based on the sensor data, determine a target object in the displayed images based on the gaze axis, and control the display to move the target object towards the central axis.

6. The HMD of claim 5, wherein the viewing location corresponds to a location of at least one eye of a wearer of the HMD.

7. The HMD of claim 5, wherein the computer is configured to determine a pupil location of the at least one eye of a wearer of the HMD from the received images.

8. The HMD of claim 5, wherein the optical system further comprises a visible light source.

9. The HMD of claim 8, wherein the display panel is configured to generate the virtual image by spatially modulating visible light from the visible light source.

10. The HMD of claim 5, wherein the infrared light source comprises an infrared light-emitting diode (LED).

11. The HMD of claim 5, wherein the camera comprises an infrared camera.

12. The HMD of claim 5, wherein the computer is further configured to record data based on the central axis, the gaze axis, the target object, and the displayed images, and to adjust the displayed images generated by the display panel based on the recorded data.

13. A non-transitory computer readable medium having stored therein instructions executable by a computing device to cause the computing device to perform functions, the functions comprising:

controlling a display to display images, the display having a central axis;

determining a gaze axis with respect to the central axis;

determining a target object in the displayed images based on the gaze axis; and controlling the display to adjust the displayed images so as to move the target object towards the central axis, wherein controlling the display to adjust the displayed images comprises moving the target object at a tracking rate and adjusting the tracking rate based on a difference between the gaze axis and the central axis.

14. The non-transitory computer readable medium of claim 13, wherein determining a gaze axis comprises:

obtaining an eye pupil image;

determining the gaze axis from the eye pupil image.

15. The non-transitory computer readable medium of claim 13, wherein determining the gaze axis comprises:

obtaining a plurality of eye pupil images; and determining a gaze axis from the plurality of eye pupil images.

16. The non-transitory computer readable medium of claim 13, wherein the functions further comprise:

recording data based on the central axis, the gaze axis, the target object, and the displayed images, and adjusting the displayed images on the display based on the recorded data.

17. The method of claim 13, wherein controlling the display to adjust the displayed images so as to move the target object towards the central axis comprises:

controlling the display to move a set of displayed images towards the central axis, wherein the set of displayed images comprises the target object.

18. A method, comprising:

displaying images on a display of a head-mounted display (HMD), wherein the displayed images are viewable at a viewing location and the display comprises a central axis;

acquiring sensor data related to the motion of the HMD;

controlling the display to display images based on the sensor data;

determining a gaze axis based on one or more images of the viewing location obtained by a camera;

determining a target object in the displayed images based on the gaze axis; and controlling the display to move the target object towards the central axis.

19. The method of claim 18, wherein determining the gaze axis comprises:

obtaining an eye pupil image;

determining the gaze axis from the eye pupil image.

20. The method of claim 18, wherein determining the gaze axis comprises:

obtaining a plurality of eye pupil images; and determining the gaze axis from the plurality of eye pupil images.

21. The method of claim 18, wherein controlling the display to move the target object towards the central axis comprises:

moving the target object at a tracking rate.

22. The method of claim 21, wherein controlling the display to move the target object towards the central axis further comprises:

adjusting the tracking rate based on a difference between the gaze axis and the central axis.

23. The method of claim 18, further comprising recording data based on the central axis, the gaze axis, the target object, and the displayed images.

24. The method of claim 23, wherein controlling the display to move the target object towards the central axis is further based on the recorded data.

25. The method of claim 18, wherein controlling the display to move the target object towards the central axis comprises:

controlling the display to move a set of displayed images towards the central axis, wherein the set of displayed images comprises the target object.

* * * * *